(12) United States Patent
Boisseau et al.

(10) Patent No.: US 9,293,310 B2
(45) Date of Patent: Mar. 22, 2016

(54) METHOD AND APPARATUS FOR MONITORING A CHARGED PARTICLE BEAM

(71) Applicant: Pyramid Technical Consultants, Inc., Lexington, MA (US)

(72) Inventors: R. Paul Boisseau, Waltham, MA (US); Andrew Dart, Swampscott, MA (US); John S Gordon, Arlington, MA (US); William P Nett, Waltham, MA (US)

(73) Assignee: Pyramid Technical Consultants, Inc., Lexington, MA (US)

( * ) Notice: Subject to any disclaimer, the term of this patent is extended or adjusted under 35 U.S.C. 154(b) by 185 days.

(21) Appl. No.: 14/215,311

(22) Filed: Mar. 17, 2014

(65) Prior Publication Data

US 2014/0265823 A1   Sep. 18, 2014

Related U.S. Application Data

(60) Provisional application No. 61/793,603, filed on Mar. 15, 2013.

(51) Int. Cl.
*H01J 47/02* (2006.01)

(52) U.S. Cl.
CPC ............ *H01J 47/02* (2013.01); *Y10T 29/49117* (2015.01)

(58) Field of Classification Search
CPC .......................... H01J 47/02; Y10T 29/49117
See application file for complete search history.

(56) References Cited

U.S. PATENT DOCUMENTS 6,437,513 B1 *   8/2002   Stelzer ................... H01J 47/02
                                                         250/283

* cited by examiner

*Primary Examiner* — Mary Ellen Bowman
(74) *Attorney, Agent, or Firm* — Intrinsic Law Corp.; Ibrahim M. Hallaj (57) ABSTRACT

An ionization chamber with spatial distribution electrode for monitor hadron beam currents used for therapeutic treatment. Ionization chamber comprises humidity control, environmental sensing and real-time correction thereof. A flexible hermetic seal provide for ambient pressure equalization. X-Y electrode planes measure Gaussian distribution of incident particle beam. Methods described herein are suitable to fabricate highly accurate, low scattering electrodes with high spatial resolutions.

19 Claims, 10 Drawing Sheets

Alignment sequence

Bonding the thin-film
electrode to the support frame

Bonding the mounted electrode
to the chamber structure

Fig. 6

Methods of establishing electrical contacts

METHOD AND APPARATUS FOR MONITORING A CHARGED PARTICLE BEAM

RELATED APPLICATIONS

This application is related and claims priority to U.S. Provisional Application No. 61/793,603 entitled, "A Method for Monitoring and Control of a Charged Particle Beam for Therapeutic Purposes" filed on Mar. 15, 2013, which is hereby incorporated by reference in its entirety.

TECHNICAL FIELD

This invention relates generally to hadron therapy. Specifically, systems and methods are disclosed for monitoring particle beam currents and multi-dimensional spatial distributions used in clinical therapies.

BACKGROUND

Radiation therapy systems can be used to provide treatment to patients suffering a variety of conditions. Radiation therapy can be used to perform selective cell destruction, useful in controlling cancers by treating tumorous tissue. An external source produces a collimated beam of radiation that is directed into the patient to the target site. A quantity of radiation can be directed into targeted tissue with the goal of damaging the targeted tissue while limiting or minimizing damage to non-targeted tissue.

The dose and placement of the dose must be accurately controlled to ensure that the tumor receives sufficient radiation and that damage to the surrounding healthy tissue is minimized. Radiation dosimetry is used to calculate and assess the ionizing radiation dose received by the human body due to external irradiation. The radiation dose may be determined during treatment planning for planning purpose, and/or during actual treatment for verification of delivery of dose.

Existing radiotherapy systems use electrons to generate the radiation beam. In such systems, the ability to control the dose placement is limited by the physics of the beam, which necessarily irradiates healthy tissue on the near-side and far-side of a target region as it passes through the patient. For particle therapy, beams of high energy charged particles, for example, protons but also heavier ions such as ionized carbon, oxygen and argon, may be used to deliver a therapeutic dose. Particle therapy offers improvements over more conventional electron and X-ray therapies by being able to deliver a dose much more precisely to a region within the body and with reduced unwanted damage to healthy tissues surrounding the region.

Proton therapy is a form of radiation therapy that uses protons to destroy targeted cells. Proton therapy can be an efficacious way to selectively destroy targeted cells because protons have unique dosimetric characteristics compared to other radiation, such as electrons or photons. Protons deposit most of their energy near the end of their path through a tissue. Because the dose provided by a proton is concentrated at a "Bragg peak" around the area where the proton stops, the dose to healthy tissue on the near-side of the target region may also be reduced. In this way, tissue on the far-side of the target region does not receive any radiation dose.

In contrast, photons deposit an exponentially decreasing amount of energy as a function of penetration depth. Thus, a proton therapy system can achieve greater targeted treatment compared to photon-based therapy (e.g., exposing targeted tissue to more radiation and/or healthy tissue to less radiation) because an operator can control a depth of penetration and dose profile of protons by selecting an initial energy of the protons. Proton irradiation requires beams to be directed to particular positions with good accuracy and with repeatable and timely control.

For particle therapy, accurate scanning and positioning of high energy particle beams is required. Until recently, proton therapy has been delivered using passive scattering. In this approach, the proton beam is expanded to subtend the entire tumor and the energy of the protons—and hence their stopping point in the tissue—is spread in range, to roughly match the tumor depth. Precise shaping of the exposure volume is provided by a specially constructed range correction compensator which provides additional range shifting to conform the distal edge of the beam to the distal edge of the tumor. This treatment approach essentially treats the entire tumor at once and, thus, is fast and yet less precise and requires the construction of a special compensator.

Lately, a more precise method called pencil beam scanning has been embraced. It offers a method of particle beam therapy for precise control and the ability to deliver a dose to the most complex volumetric shapes. In this approach, the proton beam remains narrowly collimated in a "pencil beam" and is steered in angle (deflection) and adjusted in range (energy) to deposit the dose as a small spot within the patient. For pencil beam scanning, angular deflection is typically less than ten degrees.

The spot is moved through the tumor in successive exposures until an arbitrary tumor volume has been irradiated. In combination with modulation of the beam intensity and sequential delivery of patterns at different beam energies, a desired dose distribution may be achieved. Several such exposures may be performed over a period of days or weeks in order to complete a treatment plan. This approach is potentially very accurate, but because the tumor is treated in successive exposures, is slower than the first approach. Further the small spot sizes create the risk of uneven dose placement or "cold spots" should there be patient movement between exposures.

For the foregoing reasons, it would be desirable to have systems and methods for accurately determining radiation dose and beam position while pencil beam scanning. It would also be desirable to have systems and methods for determining collimated beam profiles in two dimensions. The present disclosure contemplates the novel fabrication of a robust apparatus that provides for constant gain (or gain linearity), spatial resolution, minimal scattering of the ion beam and real time computation of peak position, width and accumulated dose, in addition to practical methods for manufacturing thereof and remedying these and/or other associated problems.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

In accordance with some embodiments, an ionization chamber comprises a first electrode plane comprising a first plurality of conductive elements and a second electrode plane substantially parallel to said first electrode plane. The second electrode plane comprises a second plurality of conductive elements orientated substantially orthogonally to first plurality of conductive elements.

According to one aspect of the invention, the ionization chamber further comprises a flexible hermetic seal, one or more environmental controls integrated into the interior of said ionization chamber. It also includes a desiccant cartridge disposed in the interior of said ionization chamber.

In accordance with some embodiments, a method for fabricating an ionization chamber electrode comprises the steps of tensioning a layer of metalized polymer onto a frame and laser ablating a plurality of conductive elements;

According to one aspect of the invention, the method disclosed forming a plurality of electrical connections corresponding to said plurality of conductive elements and providing an electrically insulating material around said ionization chamber electrode.

IN THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DETAILED DESCRIPTION

The present disclosure relates to systems and methods in the application of particle beam therapy. Specifically, methods comprise novel manufacturing of position sensing electrodes. Systems comprise environmental controls, interlocks, interfaces, and accurate monitoring of particle beams in time and space. The proceeding discussion is demonstrative of proton therapy systems; however, the present invention is not beyond the scope of other particle beams used for therapeutic purposes, such as, energetic photons, positive ions, neutrons or other hadrons.

One or more embodiments or implementations are hereinafter described in conjunction with the drawings, where like reference numerals are used to refer to like elements throughout, and where the various features are not necessarily drawn to scale.

Proton therapy is a type of external beam radiotherapy using ionizing radiation. During treatment, a particle accelerator is used to target the tumor with a beam of protons or other nuclei. These charged particles damage the DNA of cells, ultimately causing their death or interfering with their ability to proliferate. Cancerous cells are particularly vulnerable to attacks on DNA because of their high rate of division and their reduced abilities to repair DNA damage.

Due to their relatively large mass, protons have little lateral side scatter in the tissue; the beam does not broaden much, stays focused on the tumor shape and delivers only low-dose side-effects to surrounding tissue. All protons of a given energy have a certain range; very few protons penetrate beyond that distance. Furthermore, the dose delivered to tissue is maximum just over the last few millimeters of the particle's range; this maximum is called the Bragg peak.

To treat tumors at greater depths, the proton accelerator must produce a beam with higher energy, typically given in eV or electron volts. Tumors closer to the surface of the body are treated using protons with lower energy. The accelerators used for proton therapy typically produce protons with energies in the beams of therapeutic interest can range up to 250 MeV in the case of protons. By adjusting the energy of the protons during application of treatment, the cell damage due to the proton beam is maximized within the tumor itself. Tissues closer to the surface of the body than the tumor receive reduced radiation, and therefore reduced damage. Tissues deeper within the body receive very few protons so that the dosage becomes immeasurably small.

Even though penetration depth can be controlled by varying the proton energy, dose and spatial orientation must be carefully monitored to prevent the over exposure to healthy tissue. Typically, a radiation detector is disposed between the proton source and patient. The detector measures the radiation dose while minimizing proton scatter. To this end, ionization chambers are employed.

An ionization chamber is a gas-filled radiation detector. Ionization chambers are widely used for the detection and measurement of certain types of ionizing radiation: X-rays, gamma rays, alpha and beta particles. Conventionally, the term ionization chamber is used exclusively to describe those detectors which collect all the charges created by direct ionization within the gas through the application of an electric field.

An ionization chamber only uses the discrete charges created by each interaction between the incident radiation and the gas, and does not involve the gas multiplication mechanisms used by other radiation instruments, such as the Geiger-Muller counter or the proportional counter. As such, detector gain is more easily calculated based on known parameters, such as gas gap, density, etc. Ion chambers have a good uniform response to radiation over a wide range of energies.

An ionization chamber measures the charge from the number of electron ion pairs created within a gas caused by incident radiation. It consists of a gas-filled chamber with two electrodes; known as anode and cathode. The electrodes form parallel plates (Parallel Plate Ionization Chambers: PPIC) in varying configurations.

A voltage potential is applied between the electrodes to create an electric field in the fill gas. When gas between the electrodes is ionized by incident ionizing radiation, electron ion pairs are created and the resultant positive ions and dissociated electrons move to the electrodes of the opposite polarity under the influence of the electric field. This generates an ionization current which is measured by an electrometer circuit. The electrometer must be capable of measuring the very small output current which is in the region of microamperes to femtoamperes, depending on the chamber design, radiation dose and applied voltage, and the intensity of the incident radiation.

Each ion pair created deposits or removes a small electric charge to or from an electrode, such that the accumulated charge is proportional to the number of ion pairs created, and hence the radiation dose. This continual generation of charge produces an ionization current, which is a measure of the total ionizing dose entering the chamber.

The electric field also enables the device to work continuously by mopping up electrons, which prevents the fill gas from becoming saturated, where no more ions could be collected, and by preventing the recombination of ion pairs, which would diminish the ion current. This mode of operation is referred to as "current" mode, meaning that the output signal is a continuous current.

Transmission ion chambers are used ion therapy to monitor current and, more recently, spatial positioning for feedback and control purposes. Monitoring ionization chambers use a plane of horizontal stripes, a plane of vertical stripes, a total area plane (also called the integral or dose plane) and one or more high voltage (HV) planes to create an electric field.

The use of particularly high spatial-resolution structures is made more important because of the recent transition from broad-beam irradiation (double-double scattering) to scanned narrow-beam (pencil-beam scanning). To this end, the disclosed invention augments the number of ion terminating strips in by the X and Y directions. With that, the disclosed invention teaches a method to achieve a precision necessary for the increase in spatial resolution. It is noted that the present invention refers to both Cartesian coordinates (X-Y) and vertical/horizontal orientations interchangeably.

Figure 1:
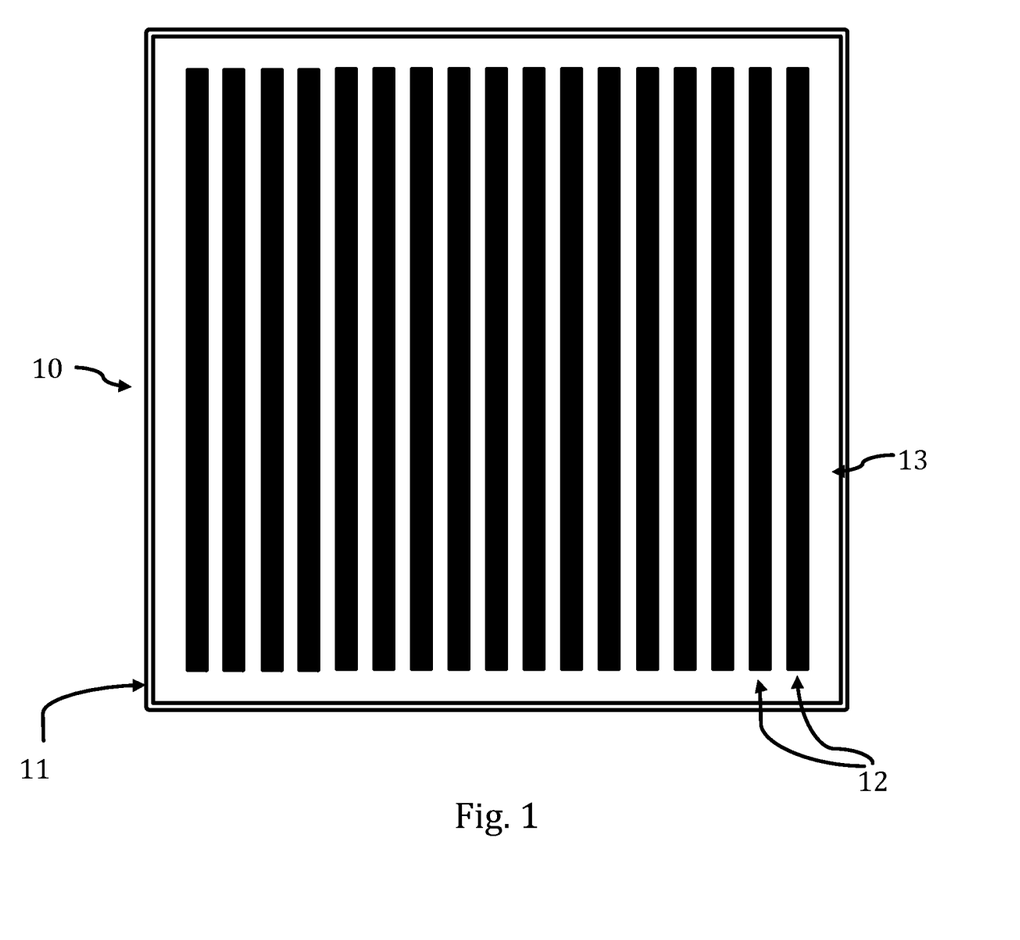
FIG. 1 illustrates an exemplary strip electrode assembly in a vertical orientation.

Turning to FIG. 1, vertical strip electrode assembly 10 comprises frame 11, film 13 and field strips 12. Assembly is performed by bonding tensioned film 13 to frame 11. Film is 25 aluminized polyimide with a thickness of 25 mm or less in some embodiments (8.5-12.5, in one or more embodiments). However, other metalized polymers (e.g., Mylar, aluminum/gold/nickel coated polyimide/polyamide) are not beyond the scope of the present invention, the specifications thereof will be discussed later. Frame 11 is made of aluminum or other suitable rigid material.

As with all the disclosed electrode structures, vertical strip electrode assembly 10 must be radiation resistant to prevent degradation. The electrode structures must also be as thin as possible to minimize scattering of the beam as it passes through the ionization chamber and energy loss in the detector. Field strips 12 are fabricated from pre-aluminized polymer film. In a preferred embodiment, the polymer is polyimide which is extremely radiation-resistant. The strength of polyimide also allows film 13 to be sufficiently thin (<~1000 A) and does not contribute significantly to beam scatter or energy loss.

The film is stretched so it remains under tension during fabrication, and during use. The advantage of processing the film in its stretched state is that no distortion is added in post-processing. If the film were patterned then stretched, the pattern would be modified and the precision compromised.

The number of field strips 12 range from 16 to 128, depending on spatial resolution. Field strips 12 are created by selectively removing the aluminum from film 13 to create a number of isolated electrodes on the insulating polymer substrate comprised by film 13. In one embodiment, the removal is performed using laser ablation. In this process, a highly-focused, nanosecond pulsed ultra-violet (UV) laser is directed onto the metal film surface. With sufficient energy density, the pulsed laser light vaporizes the metal film over an area of a few to tens of microns, leaving the substrate largely intact. The technique is capable of very high spatial accuracy, typically on the scale of a few microns. The process does not require mechanical contact with the film. Unlike alternative methods such as lithography, the material does not need to be coated, stripped, etched, etc., all of which can damage or distort the electrode film.

As part of the laser processing, alignment holes (not shown) are cut into film 13. These are precisely aligned with the electrode pattern. During the final assembly (discussed in detail later in the disclosure), these fiducial holes or markings are used to register film 13 with the support structure through the use of dowel pins. These same holes are then used to align the intermediate support structure with the overall support structure. In this way, the laser-ablated pattern can be aligned with the mechanical shell with an accuracy of <10 microns.

Figure 2:
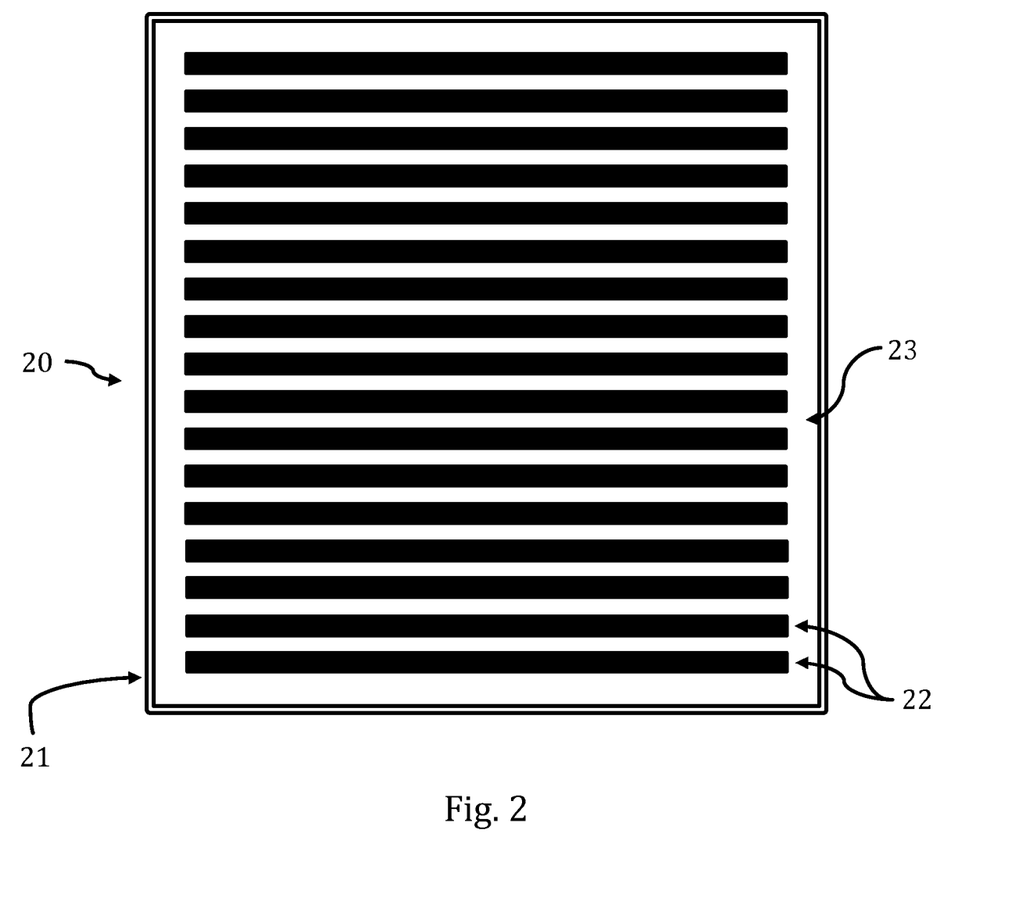
FIG. 2 illustrates an exemplary strip electrode assembly in a horizontal orientation.

FIG. 2 illustrates an exemplary strip electrode assembly 20 in a horizontal orientation. Strip electrode assembly 20 comprises frame 21, field strips 22, and film 23. Strip electrode assembly 20 is manufactured using the same method disclosed for strip electrode assembly 10, with the ostensible difference being orientation. In operation, vertical field strips 12 register the ion distribution incident on the X-axis, while horizontal field strips 22 register ions ion distribution incident on the Y-axis. In the foregoing embodiment, vertical and horizontal field strips 12, 22, respectively are ablated onto opposing faces of a single polymer substrate.

Figure 3:
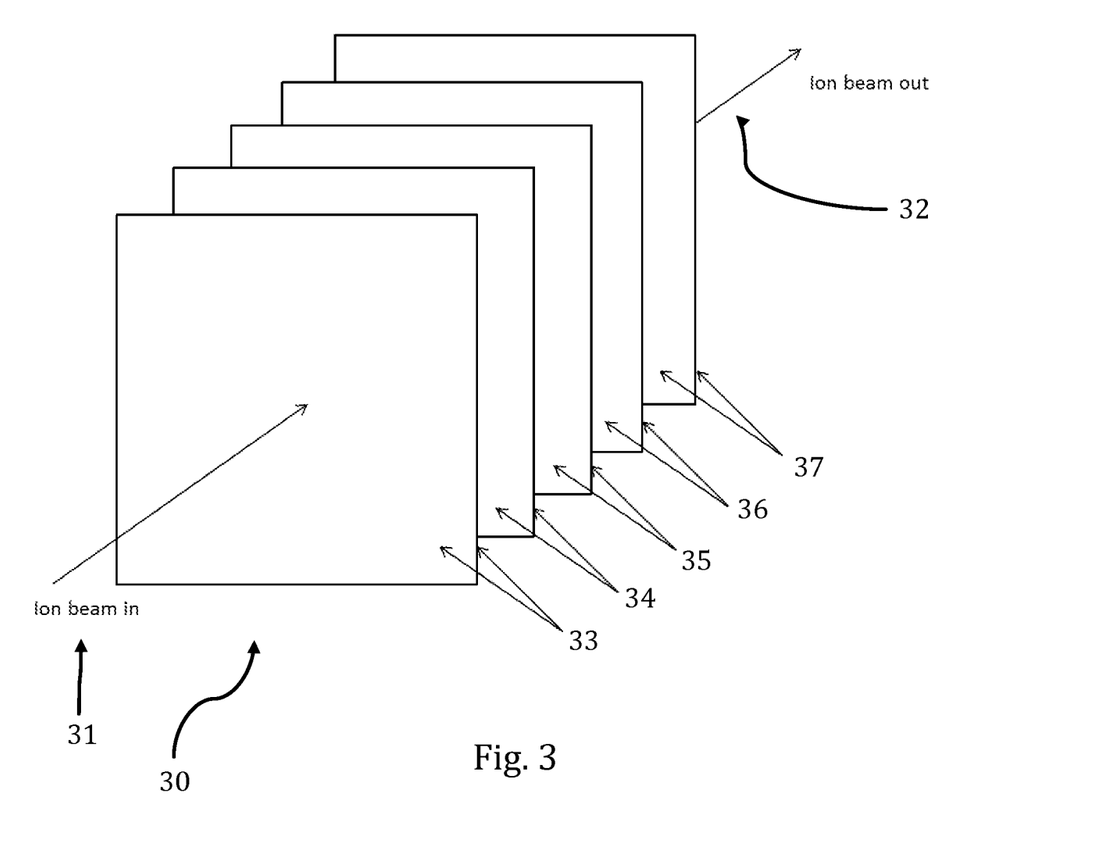
FIG. 3 illustrates an exemplary an ionization chamber subassembly heuristically depicting functionality.

FIG. 3 is an abstraction of an ionization chamber sub-assembly 30 to exemplify operation. Ionization chamber sub-assembly 30 comprises ground planes 33, 37, high voltage (HV) planes 34, 36 and X-Y electrode plane 35. X-Y electrode plane is a structure comprising X field strips and Y field strips on opposite sides, thereby minimizing the number of necessary electrode planes. HV planes are biased relative to X-Y plane thereby producing an electrostatic field with field lines similar to that of a parallel plate capacitor. In operation, particle beam 31 ingresses ionization chamber sub-assembly 30 through ground plane 33.

A gas gap disposed between HV plane 34 and X-Y plane 35 gives rise to an active region associated with an ionization event. Gas molecules in the active region become ionized after being struck by particle beam 31. Consequently, cations are pulled toward the HV 34 which acts as the cathode. Conversely, anions are drawn into X-Y electrode plane 35 (anode), pursuant to the Lorentz force albeit with thousands of small scattering events which limit velocity.

Similarly, a gas gap disposed between HV plane 36 and X-Y electrode plane 35 gives rise to an additional active region. Gas molecules in the active region become ionized after being struck by particle beam 31, after passing through X-Y electrode plane. Subsequently, cations are pulled toward the HV 36 which acts as the cathode. Conversely, anions are drawn toward X-Y electrode plane 35 (anode). Current measurements and spatial determination will be discussed later in the application. Particle beam 32 egresses ionization chamber sub-assembly 30 through ground plane 37.

HV planes 34, 36 are made from unpatterned metalized polyimide, although they may be made from any suitably radiative resistant material (rad hard) exhibiting bulk conductivity. In an alternate embodiment, A single, two-sided HV plane replaces the X-Y electrode plane 35 and vertical and horizontal electrodes (faced accordingly) replace HV planes 34, 36.

Figure 4:
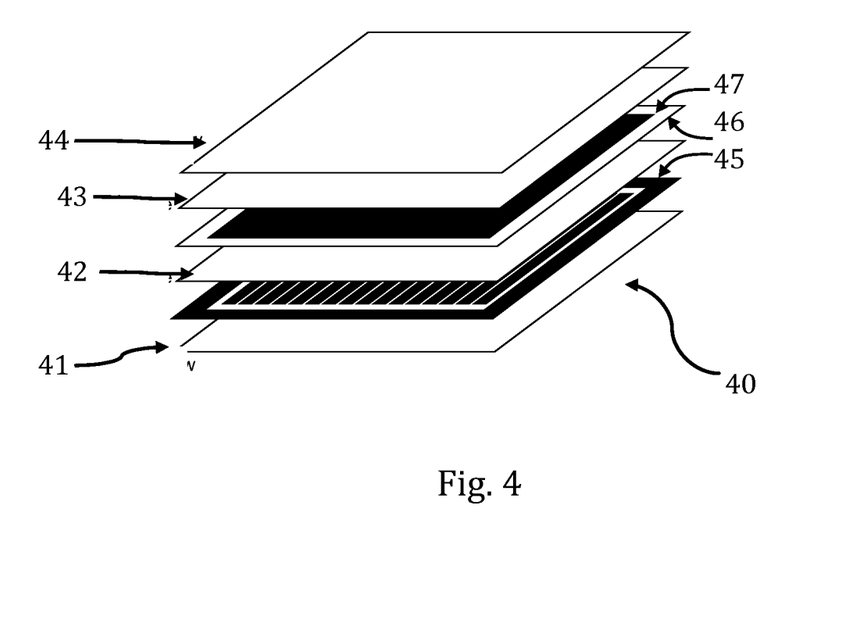
FIG. 4 illustrates an exemplary an ionization chamber subassembly heuristically depicting functionality, according to an alternate embodiment.

FIG. 4 illustrates an exemplary an ionization chamber sub-assembly 40 heuristically depicted for manufacturing, according to an alternate embodiment. In contrast to the previous embodiment where the metalized polymer is metalized on both sides, ionization chamber sub-assembly 40 comprises layers of vertical and horizontal strips planes 45, 46 respectively, interposed by layers of HV planes 42, 43. Active regions (i.e., gas gaps) are disposed between vertical strips plane 45/HV plane 42 and horizontal strips plane 46 and HV plane 43. Integral plane 47 is a single electrode that spans the entire active area of the device, and is used to measure the total beam current, independent of beam position. For reference, gas tight windows 41, 44 are also illustrated.

Figure 5:
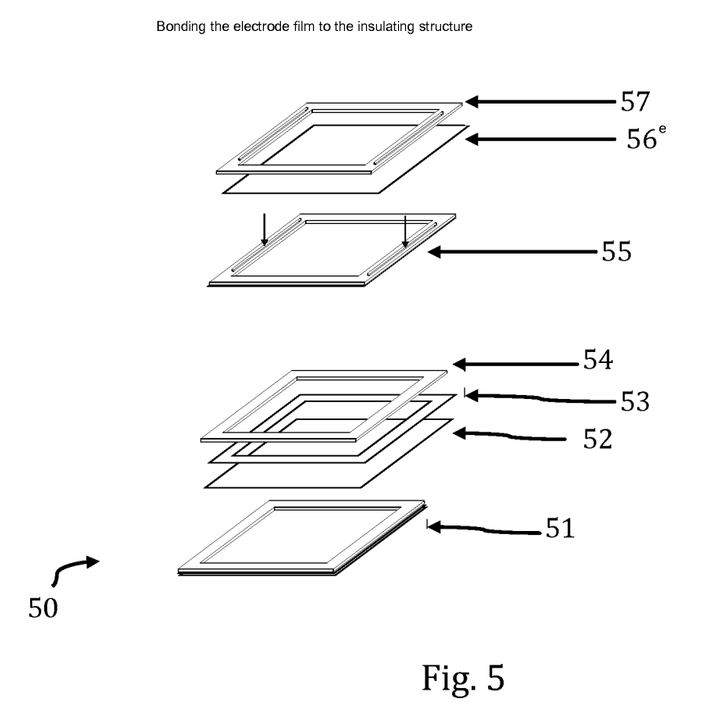
FIG. 5 illustrates an exemplary construction of a film electrode bonded to a frame.

The response of the ion chamber is proportional to the gas gap. Therefore, spatial uniformity of response requires that the electrode planes defining the gas gaps be flat and parallel to better than 1% of the electrode interplanar spacing (3-10 mm typ). FIG. 5 illustrates an exemplary construction 50 comprising film electrodes 52, 56 bonded to an insulating structure. The present invention discloses two methods for reducing the errors due to the attachment of film to support structure.

First, electrode film 56 is bonded to the support structure 57 using epoxy adhesive. The adhesive is applied though slots in the substrate, filled from the non-film side. Arrows portray the application direction on the bonded structure 55. This attaches the film electrode 56 to the support structure 57 but adds no material to the interface therebetween.

An alternate method of bonding the film to the substrate uses an adhesive between the electrode film and the support structure. Electrode film 52 is bonded to the support structure 54 using partially cured epoxy 53. Partially cured epoxy comprises very thin layers of so-called "B-staged" epoxy in sheet form. The use of such films allows the creation of a very precisely controlled adhesive thickness, since the layer thickness is determined by the well-controlled epoxy film thickness and not by the application method. The resultant structure 51 is assembled, placed under light pressure and heated until the epoxy bonds and cures. The resulting bond is highly uniform and reproducible, exhibiting minimal creep during the curing stage.

As discussed previously, electrode film is fabricated from pre-metallized polymer film under tension. The resulting surface is determined by the shape of the supporting structure, which can be machined to a high degree of flatness. The combination of these methods leads to very flat, parallel electrode planes engendering stability of the response over time under varying environmental conditions.

Figure 6:
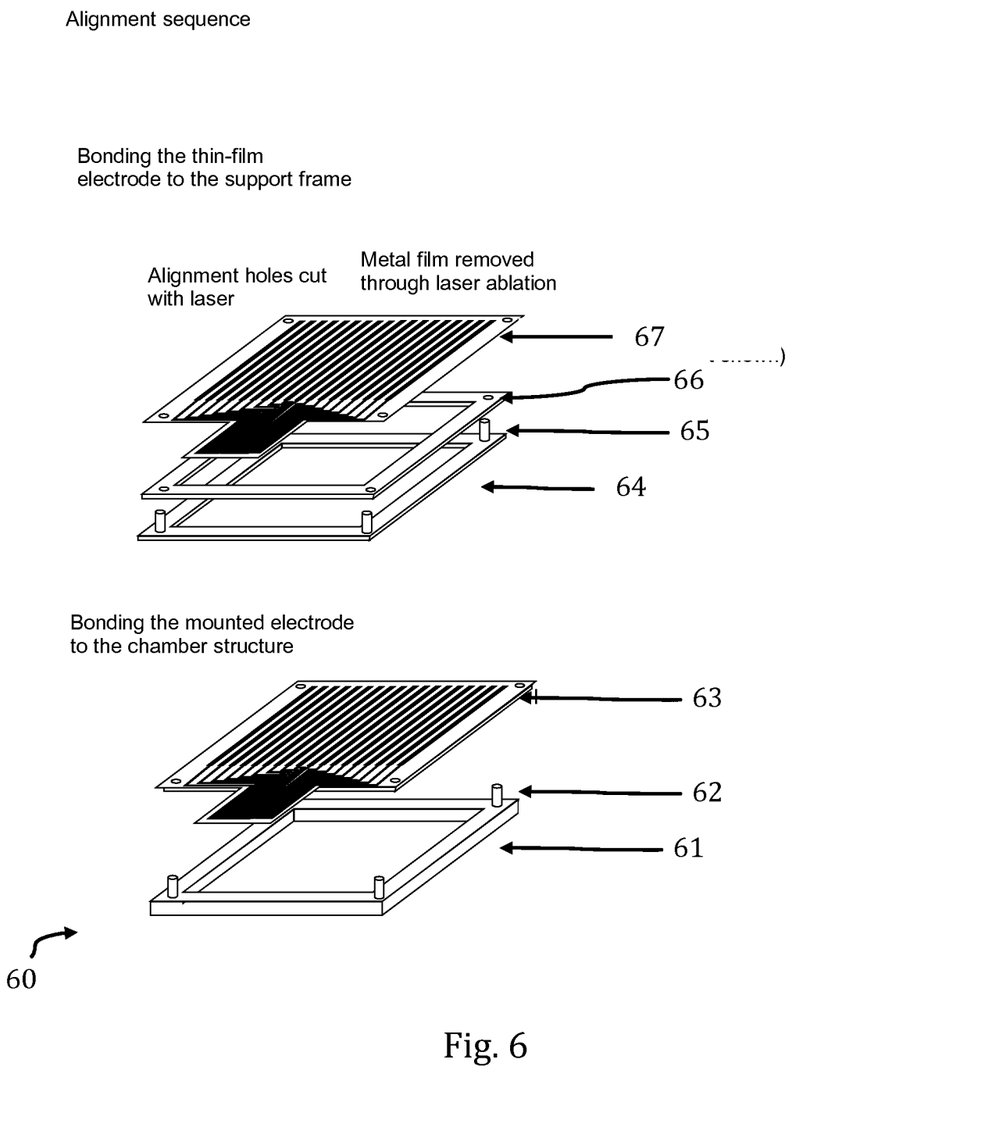
FIG. 6 is demonstrative of an alignment sequence for bonding a strip electrode assembly to a ionization chamber structure.

FIG. 6 is demonstrative of an alignment sequence 60 for bonding a strip electrode assembly 63 to a ionization chamber structure. Alignment holes are cut into tensioned electrode film 67 antecedently. Electrode film 67 is bonded to support frame 66 using the alignment pins 65 comprised by temporary alignment jig 64. After curing, temporary alignment jig 64 is removed resulting in electrode assembly 63. Electrode assembly 63 is then bonded to ionization chamber structure 61 using alignment pins 62 through extant alignment holes.

Figure 7:
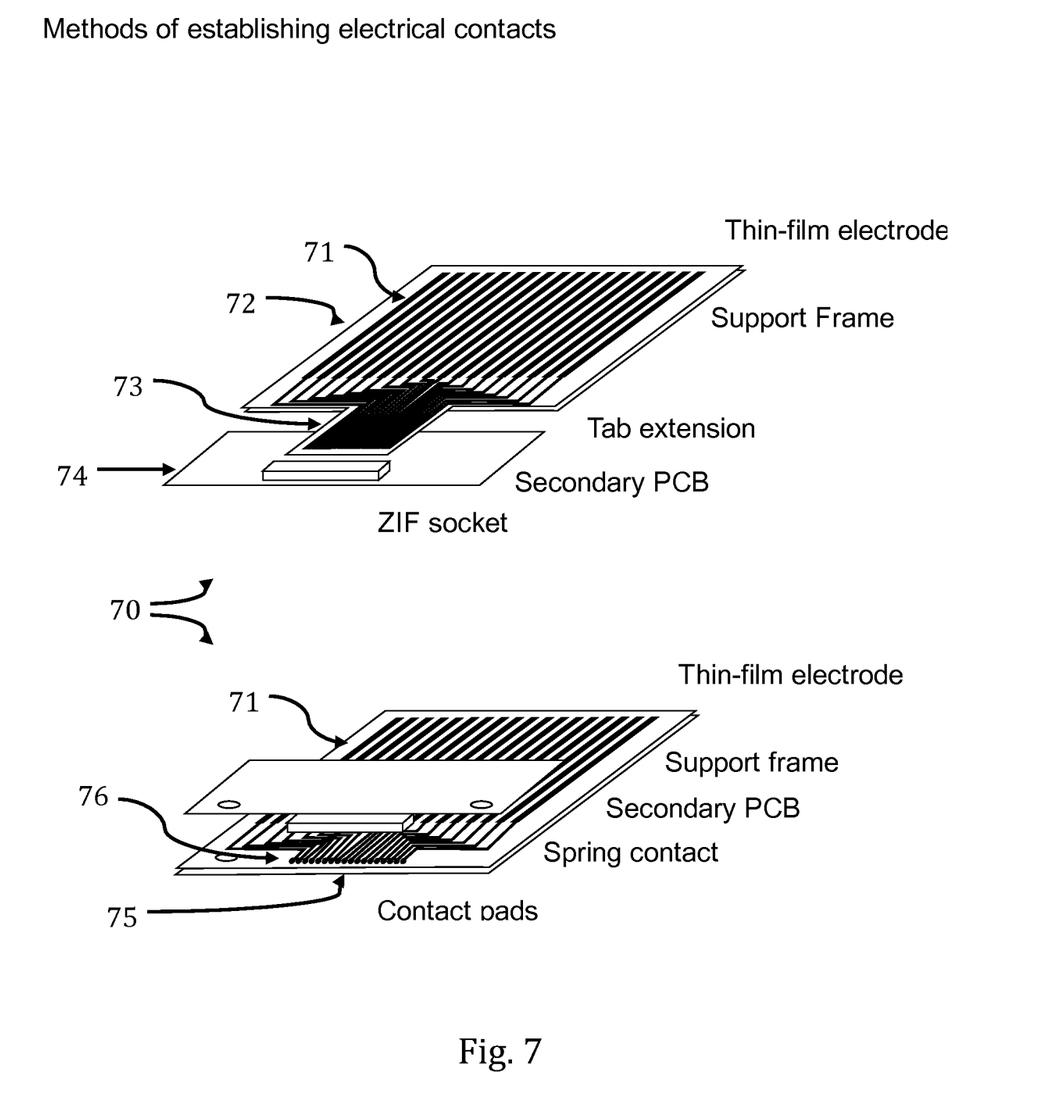
FIG. 7 is demonstrative of a sequence for establishing metal contacts to a strip electrode assembly.

FIG. 7 is demonstrative of a sequence for establishing metal contacts to a strip electrode assembly 70. Electrode assembly 70 comprises support frame 71, printed circuit board (PCB) 74 and electrode strips 71 coupled to tab extension 72. One method for electrical communication to the electrode strip is to adhere conductive contacts to delicate electrode strips. The present embodiment employs the following methods.

Tab extension 72 extends outside of the electrode strips 71 carrying individual traces for the individual electrodes. Tab extension 72, properly dimensioned and reinforced, is inserted into a zero-insertion force (ZIF) connector. ZIF connector is mounted to a conventional printed circuit board 74, and the signals distributed in a conventional manner.

In a more robust alternate embodiment, signal traces are brought outside of the active area but still within the envelope of the insulating support structure. The traces, structured into appropriate contact pads 75, can then be contacted with a spring-loaded contact connector 76, which is brought into secure contact with the support structure. Such a spring connector 76 can be mounted to a conventional printed circuit board, and the signals distributed in a conventional manner.

Figure 8:
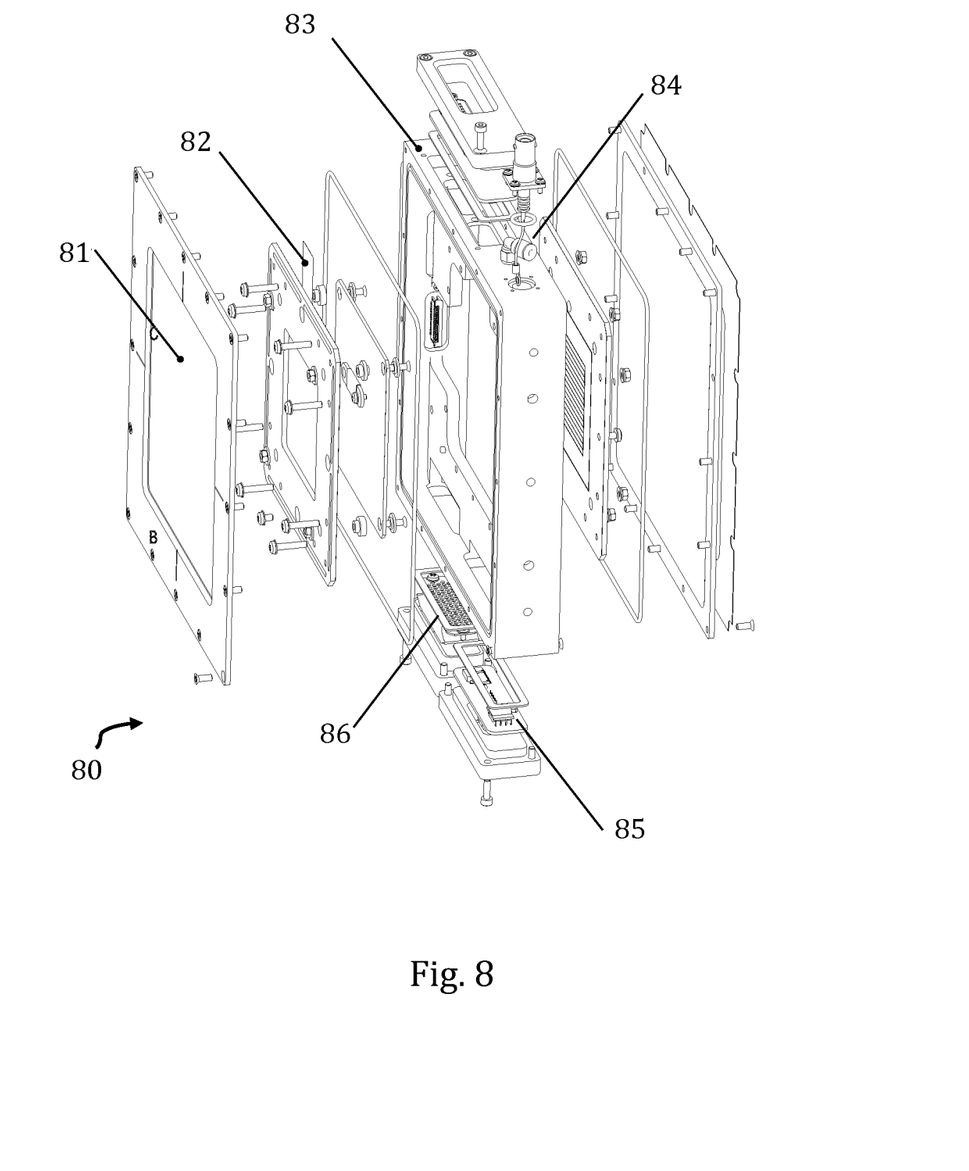
FIG. 8 illustrates the exploded view of an exemplary ionization chamber.

FIG. 8 illustrates the exploded view of an exemplary ionization chamber 80. Ionization chamber 80 comprises hermetic window 81, ZIF tab 82, outer chassis 83, gas flow inlet 84, integrated environmental sensors 85, and desiccant cartridge 86. Ionization chamber 80 gain is proportional to the density of the fill gas.

Some designs utilize sealed construction with the ground electrodes making up the outer shell of the hermetic chamber. The amount of gas in the gap is therefore constant. To prevent spatial non-uniformity due to variations in outside pressure, these structures must be made thick thereby increasing particle scattering. Other ionization chamber design are non-hermetic. Non-hermetic chambers are vented allowing equalization of ambient temperatures and pressures. Variations in pressure and temperature are compensated by using external sensors which extrapolate measurements in the interior of the ionization chamber. This can introduce errors if the conditions at the point of measurement does not accurately represent the conditions inside the ion chamber.

The present invention discloses a gas-tight configuration but uses very thin membranes for sealing. Hermetic window 81 flexes as ambient pressure changes. Similar to the electrode substrate, hermetic window 81 is made of radiative resistant polymer. However, the sealing film is not an active electrode. Because sealed gas flows freely throughout the interior, internal electrodes remain flat. Interior gas density varies as a function of ambient pressure.

In one or more embodiments, integrated environmental sensors 85 (temperature, pressure and humidity) are disposed on the interior of ionization chamber 80. Variations of internal conditions are accurately determined and compensated for in the software of the control circuit which will discussed later. The fill gas may be atmospheric air, or any other suitable gas mixture. The chamber is hermetically sealed, but an external source of fill gas can be used through the use of gas flow inlet 84. The gas flow outlet port is not shown. Variations in pressure and temperature in any externally supplied fill gas can be measured and compensated in the same manner as with the fully-sealed configuration.

A replaceable desiccant cartridge 86 maintains a very low humidity of the chamber fill gas. This mitigates arcing in the chamber and instability in the signal. The desiccant can be silica, soda lime or other suitable material. A consistent low humidity also ensures that any humidity-dependent effect on the chamber sensitivity are minimized and made consistent over time. A sensor integrated into the chamber measures the humidity of the fill gas, and thus indicates if the desiccant should be replaced.

With the use of high current density beams, a nonlinear effect in gain will occur due to recombination of the ion-electron pairs. Recombination effects become significant with high intensity particle beams and are a particular problem for pulsed beams. Real-time correction for recombination losses is made using the measured values of beam current and beam shape to determine the beam current density. The amount of recombination as a function of beam current can be determined by independent measurements. The system is thereby able to measure accurately over a wider dynamic range of beam current.

Figure 9:
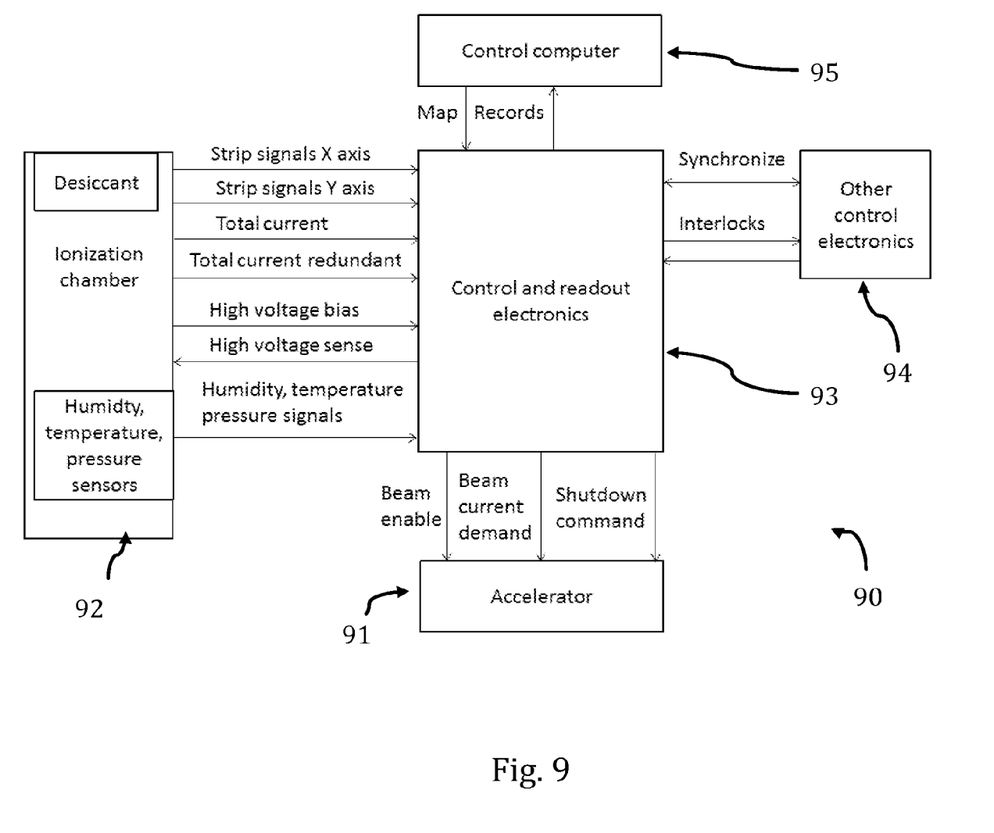
FIG. 9 illustrates an exemplary block diagram for monitor/control circuitry.
Figure 10:
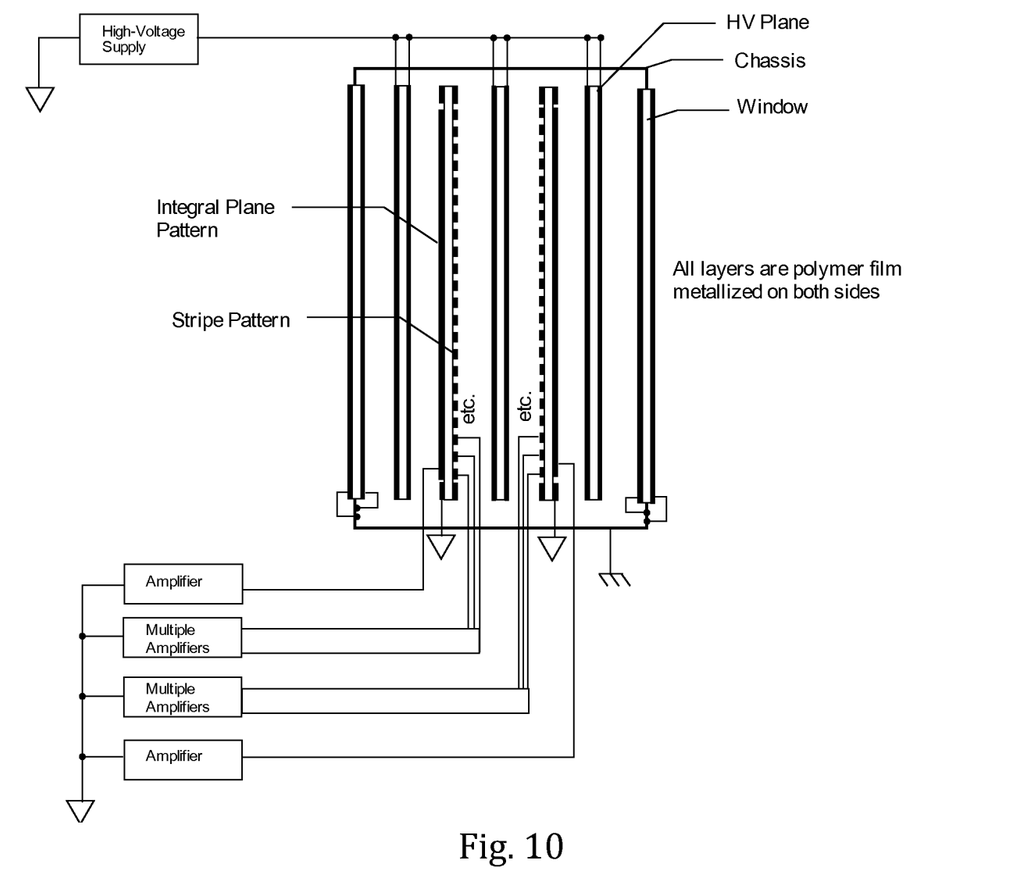
FIG. 10 illustrates an exemplary equivalent circuit whose signals are used in current, gain and dose calculations.

FIG. 9 illustrates an exemplary block diagram 90 for monitor/control circuitry. Control and readout electronics 94 are in electrical communication with ionization chamber 92, accelerator 91, control computer 95 and other control electronics 93. Control and readout electronics 94 measure the current signals from the ionization chamber 92. Control and readout electronics 94 also receive signals from humidity, temperature and pressure sensors, in addition to high voltage readback.

Using these signals and values computed from them, the electronics determines whether the dose required by a map received from a control computer has been reached, and if so, send a signal to the accelerator beam source to disable the beam. It may also change the intensity of the beam in order to improve the accuracy of the dose delivery. It will cause the irradiation to be halted by using the beam enable signal plus various levels of interlock if values of beam current, beam position, beam width, high voltage read-back are out of tolerance. It will cause the irradiation to be halted by using the beam enable signal plus various levels of interlock if it suffers an internal failure. The electronics can coordinate execution of the irradiation map with other similar devices, and a series interlock chain can ensure that any unit in the chain can cause the irradiation to halt.

The gas density is a known function of the temperature and pressure through the ideal gas law. The gain of the chamber is a linear function of the density, where gain is the measured current divided by the actual beam current. Control software is used to actively compensate for variations in the measured temperature and pressure.

Connection to the high voltage plane is done using two electrical paths. The first connects to the voltage source and the second returns the voltage to the control electronics, to enable a positive sensing that bias voltage has reached the plane. Demountable connections to the position-sensing strips (X-Y) are made using zero insertion force (ZIF) connectors to allow convenient disassembly of the ionization chamber for servicing.

Readout and control electronics are provided which combine the parallel readout of the position strips, readout of the total current electrode, readout of temperature and pressure, computation of values based on these readings, comparison of these values with predetermined nominal values, and operation of interlocks in the event that acceptable bounds are exceeded. These functions are integrated in a single electronics unit to avoid the delays and risks associated with communicating raw data to other electronics or to computer systems.

One or more embodiments utilize a pair of XY structures transverse to the particle beam as part of a monitoring system during treatment. This allows not only the beam intensity profile to be to be extrapolated in 2 dimension but 3 dimensional trajectory as well. Alternatively, a pair of ionization chambers separated along the direction of the undeflected ion beam can be used. This will produce two measures of the transverse position of the beam provided they both sense in the relevant transverse direction.

Using the known spacing and trigonometric calculation, this arrangement allows the angle of the beam relative to the undeflected beam axis to be measured. If both of the ionization chambers are sensitive in the two orthogonal transverse directions, then the complete trajectory of the ion beam can be reconstructed. The electronics provide sufficient independent parallel measurement channels, for example 64 or 128, to read out at least one position-sensing axis. The ability to accurately determine the beam trajectory allows the position of the beam at the patient to be determined.

The electronics provides an additional measurement channel to read out a total current measuring electrode at high sampling rate. The electronics automatically checks that all signal channels respond in a pre-defined manner when high voltage bias is applied and the ionization chamber capacitance is charged. This validates the operation of each channel without the need for an independent protocol. The electronics computes accumulated beam current, and thus dose to the patient. When the required dose is reached as measured on a total current electrode, the electronics unit can send a signal to the source of the beam current, generally a particle accelerator, to turn off the current.

The electronics may also send a signal directly or via an intermediary device to change the beam intensity so as to give finer control and thus more accurate dose delivery. The electronics computes the position and width of the beam at high rate using an optimized algorithm, implemented in a field-programmable gate array (FPGA) that fits a Gaussian distribution to the data without iteration. The algorithm achieves this by taking logarithms of the background-corrected data, fitting a weighted second-order polynomial to the transformed data, then computing the amplitude, mean and standard deviation of the corresponding Gaussian distribution. Other functional fits can also be implemented when appropriate.

The electronics has an integrated highly-stable and accurately-known calibration current source which can be used to maintain the measurement accuracy of the signal readout channels by an automated calibration process. The electronics can supply high voltage bias to the ionization chamber and monitor the voltage level. It can also monitor the sampled voltage returned from the ionization chamber to confirm that the chamber is actually receiving the bias voltage. The electronics can receive a sequential list of nominal values (map) for beam dose, position, width and other parameters.

During irradiation it compares these with the measured and computed values, using digital filtering as necessary for noise reduction, and decides whether the irradiation is proceeding within bounds. If the bounds are exceeded, it signals the source of the ion beam one or more direct hardware connections to stop the irradiation. The electronics monitors its own state of health using a watchdog system and redundant complex programmable logic device (CPLD) hardware, and also signals to stop the ion beam delivery with a safety-rated relay if a failure occurs. The electronics supports direct links to other similar devices to permit coordinated stepping through map entries, and redundant interlocking via series connection of relays for enhanced safety.

High beam intensities produce nonlinearity due to charge recombination. The amount of recombination can be estimated at any current density from theory or through direct measurement. Since the ionization chamber does allow the first-order beam current density to be measured, it is possible to actively compensate for recombination loss in real-time. This is done by exploiting the known relationship between beam current density and recombination loss. Correcting for nonlinearities provide for measurement of high-current density beams and pulsed beams in particular accurately in real-time, even in the presence of temporal variations in beam current density.

The embodiments described and illustrated herein are not meant by way of limitation, and are rather exemplary of the kinds of features and techniques that those skilled in the art might benefit from in implementing a wide variety of useful products and processes. For example, in addition to the applications described in the embodiments relating to particle therapeutic treatments, the present invention may be used in other ion implantation technologies, such as, semiconductor fabrication. It is also to be appreciated that the present exemplary embodiments are also amenable to other like applications. Furthermore, the recitation of proton and ion-electron pairs is exemplary. However, therapies using heavy ions (e.g., carbon, oxygen, argon etc.), photons, neutrons and hadrons in general are not beyond the scope of the present invention.

The present invention should not be considered limited to the particular embodiments described above, but rather should be understood to cover all aspects of the invention as fairly set out in the attached claims. Various modifications, equivalent processes, as well as numerous structures, materials and unforeseen technologies to which the present invention may be applicable, will be readily apparent to those skilled in the art to which the present invention is directed upon review of the present disclosure. The claims are intended to cover such modifications and equivalents.

What is claimed is:

1. An ionization chamber comprising:
    a first electrode plane comprising a first plurality of conductive elements;
    a second electrode plane substantially parallel to said first electrode plane, the second electrode plane comprising a second plurality of conductive elements oriented substantially orthogonally to first plurality of conductive elements;
    a flexible hermetic seal preventing mixing of a gas within said ionization chamber with surrounding ambient gases;
    one or more environmental sensors integrated within said ionization chamber and sensing one or more corresponding aspects of said gas within said ionization chamber; and
    a desiccant cartridge disposed in the interior of said ionization chamber.

2. The ionization chamber of claim 1, further comprising current sensors electrically coupled to said first and second pluralities of conductive elements.

3. The ionization chamber of claim 1, wherein said first and second electrode planes comprise a metallized polymer.

4. The ionization chamber of claim 3, wherein said first and second pluralities of conductive elements are created by laser ablation of polyimide film.

5. The ionization chamber of claim 1, further comprising a gas flow valve.

6. The ionization chamber of claim 1, further comprising one or more integral plane electrodes which define gas gaps for measuring directly the total current of the particle beam.

7. The ionization chamber of claim 1, further comprising one or more conductive planes offset from said first and second electrode planes thereby creating a gas gap.

8. The ionization chamber of claim 1, wherein said one or more environmental sensors comprises a temperature sensor.

9. The ionization chamber of claim 1, wherein said one or more environmental sensors comprises a pressure sensor.

10. The ionization chamber of claim 1, wherein said one or more environmental sensors comprises a humidity sensor.

11. A method of fabricating an ionization chamber electrode, comprising:
    tensioning a metalized polymer sheet onto a rigid frame;
    ablating a conductive material on said metalized polymer sheet to form a plurality of conductive elements disposed on a surface of said metalized polymer sheet;
    connecting a plurality of electrical connections corresponding to said plurality of conductive elements; and,
    providing an electrically insulating material around said ionization chamber electrode.

12. The method of claim 11, further comprising the step of disposing a conductive plane proximal to said metalized polymer sheet.

13. The method of claim 11, wherein, the metalized polymer sheet comprises a polyimide.

14. The method of claim 11, said ablating step comprising laser ablation.

15. The method of claim 11, further comprising providing a fill gas into an interior of said ionization chamber and monitoring at least one aspect of said fill gas from within said ionization chamber while said fill gas is in said ionization chamber.

16. The method of claim 15, comprising monitoring at least a temperature, pressure or humidity level of said fill gas from within said ionization chamber while said fill gas is in said chamber.

17. The method of claim 11, said tensioning comprising pre-stretching said metalized polymer sheet by placing said sheet between a rigid frame over a rigid pedestal and applying strain to said sheet in a plane of said sheet.

18. The method of claim 11, said ablating step comprising forming a plurality of elongated and substantially parallel conducting lines on a surface of said metalized polymer sheet.

19. The method of claim 11, further comprising determining a position and orientation of an incident ionized beam penetrating said ionization chamber by registering an electrical signal generated by at least one of said conductive elements.

* * * * *